United States Patent
Abraham-Fuchs et al.

(10) Patent No.: US 6,261,239 B1
(45) Date of Patent: Jul. 17, 2001

(54) DEVICE FOR ACQUIRING AND EVALUATING DATA REPRESENTING COORDINATIVE ABILITIES

(75) Inventors: Klaus Abraham-Fuchs, Erlangen; Thomas Birkhoelzer, Weisendorf; Hartwin Hufnagel; Kai-Uwe Schmidt, both of Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/416,099

(22) Filed: Oct. 12, 1999

(30) Foreign Application Priority Data

Oct. 12, 1998 (DE) ............................................. 198 46 898

(51) Int. Cl.$^7$ .................................................. A61B 13/00
(52) U.S. Cl. ........................................ 600/558; 600/300
(58) Field of Search ..................................... 600/558, 300

(56) References Cited

U.S. PATENT DOCUMENTS

| | | | | |
|---|---|---|---|---|
| 3,747,589 | * | 7/1973 | Harrison et al. | 600/558 |
| 4,169,592 | * | 10/1979 | Hall | 600/558 |
| 5,344,324 | * | 9/1994 | O'Donnell et al. | 600/558 |
| 6,113,538 | * | 9/2000 | Bowles et al. | 600/558 |

FOREIGN PATENT DOCUMENTS

| | | |
|---|---|---|
| 2 316 346 | 10/1974 | (DE) . |
| 38 29 885 | 3/1990 | (DE) . |
| 196 33 866 | 2/1998 | (DE) . |

OTHER PUBLICATIONS

Brochure for Nintendo® Entertainment System.

* cited by examiner

Primary Examiner—John P. Lacyk
Assistant Examiner—Brian Szmal
(74) Attorney, Agent, or Firm—Schiff Hardin & Waite

(57) ABSTRACT

A device for the acquisition of coordinative abilities of a test person, allows different tests that test different coordinative abilities of the test person to be executed with the aid of a control unit. The control unit evaluates the individual test results and combines them to form a relevant quantitative overall assessment of the coordinative competence of the test person. This overall assessment is presented via a corresponding output unit, such as a screen.

30 Claims, 2 Drawing Sheets

DEVICE FOR ACQUIRING AND EVALUATING DATA REPRESENTING COORDINATIVE ABILITIES

BACKGROUND OF THE INVENTION

1. Field of the Invention

The present invention is directed to a device for acquiring and evaluating data representing coordinative abilities of a test person.

2. Description of the Prior Art

Coordinative abilities are the abilities for the control, or purposeful control, of human motion and are together referred to as coordinative competence. The coordinative competence can be divided into different aspects, i.e. it can be divided into coordinative abilities as sub-areas of the coordinative competence, such as, for example, reactivity, rhythmization ability, eye-hand-coordination ability, eye-foot-coordination ability, balance and differentiation ability of a person. In studies, coordinative competence has proven to be one of the most important parameters for an independent life of a person at an advanced age.

Systematic test methods for identifying coordinative competence, which can be executed by the test subject himself or herself, are not known. A regular "measurement" or acquisition of coordinative competence, among other things, is important in order to be able to make progress in training or therapy quantitatively apparent so as, for example, to increase the motivation of the test person. Further, the present state of health of the test person could be acquired by regularly monitoring coordinative competence, so that the degree of danger of the test person concerning a fall, for example, can be determined. Further, it therefore could be determined whether coordinative competence is impaired by specific factors that momentarily exist, such as an acute illness.

At the moment, tests of coordinative abilities are only carried out in the context of scientific studies, whereby a series of tasks are executed by the test persons under the observation of a caregiver. The caregiver subsequently evaluates these tasks manually.

SUMMARY OF THE INVENTION

An object of the present invention is to provide a device for identifying coordinative abilities of a test person, which enables an automatic assessment of the coordinative competence, or the coordinative abilities, of the test person.

The above object is achieved according to the invention by conducting a number of tests that are appropriate for the acquisition of different coordinative abilities of a test person, controlled by a test device. The test results are automatically processed by the inventive device and are combined to a quantitative overall assessment, i.e. they are combined to a relevant assessment factor, which is supplied as an output. This assessment factor, which is the overall assessment of a number of coordinative abilities, therefore represents a measure for the coordinative competence of the test person, so that his or her coordinative competence is reliably evaluated.

The inventive device is fashioned so that it enables an automatic selection or interactive selection of the tests to be carried out, with at least two different coordinative abilities, or sub-areas of the coordinative competence, are tested. The test implementation can be automatically acquired (by sensors, switches or the like for example) and/or can be interactively acquired (by input of the test results via input menus). The test results and/or the final result, i.e. the overall assessment factor of the coordinative competence of the test person, are advantageously visualized, i.e. they are presented via a display or a monitor of the inventive device.

The tests of the device are particularly designed such that reactivity, rhythmization ability, eye-hand-coordination ability, eye-foot-coordination ability, balance and differentiation ability of the test person can be separately tested as coordinative abilities of the test person.

The inventive device therefore enables computer-supported acquisition and/or evaluation of coordinative competence, and the individual test methods, which are provided or selected by the device are particularly executed directly by the concerned test person, so that participation of a trained test administrator not necessarily required. Therefore, by means of the inventive device, training progress can be determined during a therapy regimen and any danger to the health of the test person, due to lacking coordinative competence can be determined.

DESCRIPTION OF THE PREFERRED EMBODIMENTS

Figure 1:
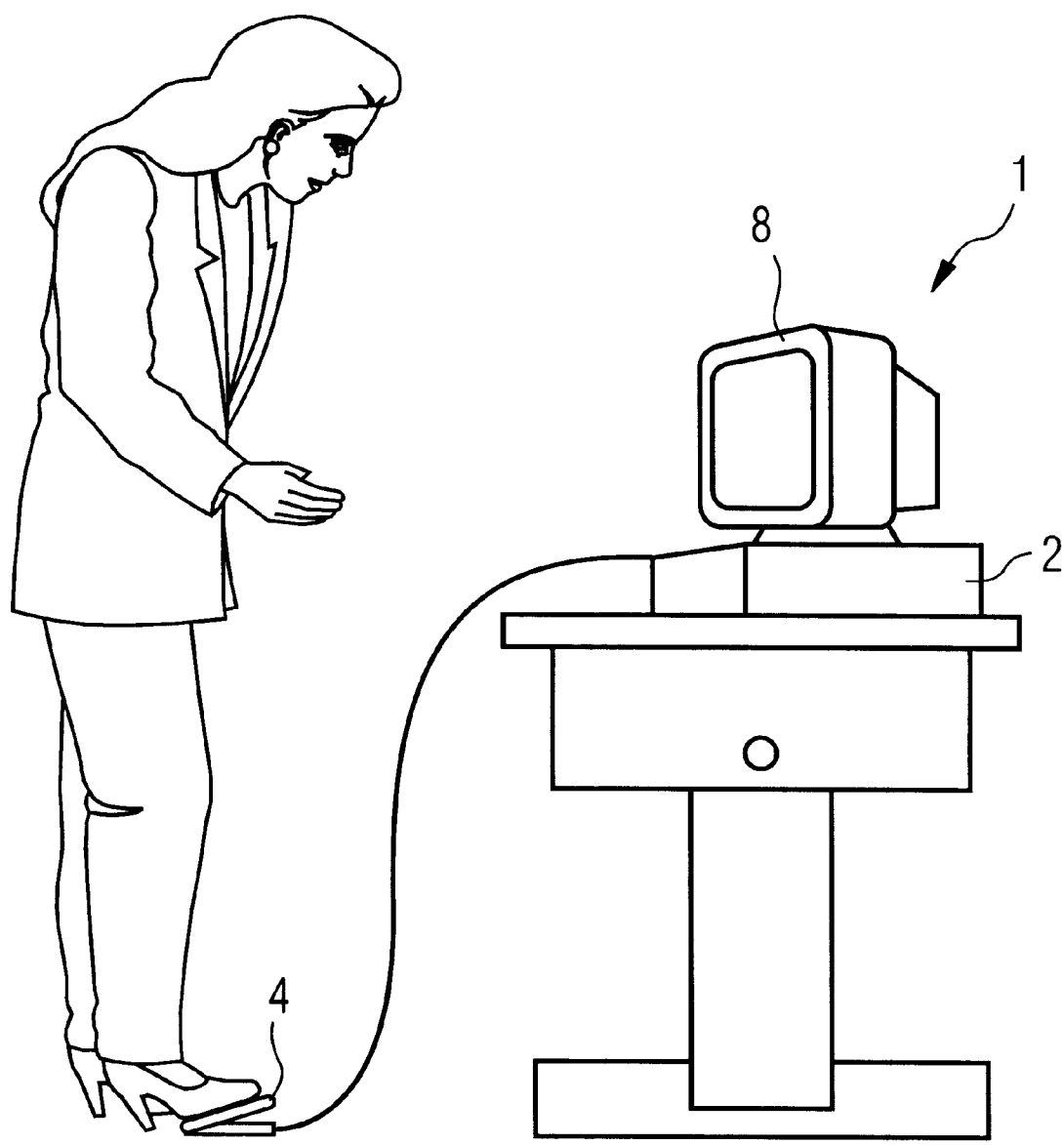
FIG. 1 schematically shows the basic structure of an exemplary embodiment of an inventive device.

The device shown in FIG. 1 has a control unit 2 that is fashioned as a personal computer and a screen 8, which serves the purpose of visualizing specific data of the control unit 2. A foot switch 4 is connected to the central control unit 2 via a line, the foot switch 4 being shown in FIG. 1 as an exemplary representative of any type of sensors, switches or other input devices that can be connected to the central control unit 2. For example, the foot switch 4 can be particularly appropriate for a test of the eye-foot-coordination of a test person, whereby a specific task to be executed by the test person is, in this case, prescribed at the screen 8; and the task must be executed with the foot switch 4 of the test person. The central control unit 2 evaluates the accuracy of the execution as measure for this eye-foot-coordination. As will be explained in greater detail below with the aid of FIG. 2, further coordinative abilities of the test person can be automatically tested and acquired using other switches, sensors or input devices. In particular, reactivity, rhythmization ability, eye-hand-coordination ability, balance or differentiation ability can be tested.

The functioning of the device shown in FIG. 1 is as follows.

Using the device 1 shown in FIG. 1, different sub-areas of the human coordinative competence can be tested, i.e. different coordinative abilities of a test person can be tested and the corresponding test results can be automatically evaluated. For this purpose, the central control unit 2 has a memory in which the data relevant for the execution of the different tests are stored, so that the available tests with corresponding information can be displayed via the screen 8 of the test person or the caregiver.

A selection of the tests that are actually to be carried out subsequently ensues; this selection of the different tests can be automatically carried out or can be interactively carried out. Given the interactive selection version, the test person or the caregiver selects the desired test exercises using a mouse or keyboard connected to the central control unit 2.

In contrast thereto, given an automatic selection, the central control unit 2 selects the test exercises to be executed. The automatic selection can ensue particularly randomly from a list of equivalent tests, so that the central control unit 2 selects a test exercise, for example, from a number of test exercises for testing reactivity of the test person. As warranted, this automatic selection can be based on a pre-selection that is manually made by the test person or the caregiver, so that the control unit 2 merely presents test exercises that were previously pre-selected by the test person or the caregiver. The advantage of the automatic selection of the tests to be carried out is that the central control unit 2 can take the previous health history of the respective test person into account in the selection of the test exercises. Thus, the central control unit 2 can take health data into consideration for example, which health data indicate the general fitness or earlier illnesses of the respective test person given the automatic selection. Thus, the overall test for measuring coordinative competence of the test person can be automatically adapted to the individual needs of the test person in an optimal way.

After the test exercises actually to be carried out are determined, test instructions regarding the individual test exercises are presented via the screen 8, these test instructions supporting the test person with respect to carrying out the respective exercise. Moreover, the device can also present further test instructions, in the form of prescribed tact signals or prescribed speeds for example, for carrying out the individual test exercises. Preferably, the device is equipped with a multi-media auxiliary function that is arbitrarily retrievable by the test person or a caregiver and that supports the test person or the caregiver with respect to the execution of the individual test exercises by text output and/or speech output or by playing videos, for example.

The test implementation and the test results can, in turn, be automatically acquired and/or can be interactively acquired by the device. In the first version, as already been explained, a number of sensors, switches or other input devices are coupled with the central control unit 2, these sensors, switches or other input devices supplying corresponding measuring signals to the control unit 2 during the execution of the individual test exercises. In the second version, the test person or caregiver himself enters the test results in the form of corresponding numerical values for example via the keyboard or the mouse, and the input can be facilitated by input menus.

The central control unit 2 evaluates the test results, acquired in this way, of the individual, executed test exercises and combines them to a single numerical value, to a overall assessment factor in order to receive a quantitative statement with respect to the coordinative competence of the respective test person. This can ensue according to a prescribed algorithm that is essentially defined by the software of the central control unit 2. Given the calculation of this overall assessment factor, apart from the test results of the individual test exercises, health data of the respective test person can, in turn, be considered in order to enable an assessment and evaluation of the test results, with the assessment and evaluation being individually adapted to the respective test person. Thus, the age of the test person, earlier illnesses, i.e. the previous health history, the intake of medication etc. for example can be included in the assessment of the coordinative competence. The central control unit 2 contains this information or health data in the form of patient data or test person data, which are usually stored in a data bank, so that the data can be accessed without any problems. Subsequent to the calculation of the overall assessment factor of the coordinative competence of the test person, the corresponding data and the test results can be stored in a memory of the central control unit 2 and can be present via the screen 8. It is possible to identify and show trends over a longer period of time by storing the test results and the overall assessment factor, so that, for example, the development of the overall assessment factor of the coordinative competence of the test person can be followed over a longer period of the therapy in order to be able to correspondingly intervene, on time, in the therapy or treatment, if necessary. Moreover, the central control unit 2 is coupled with a data transmission interface, which enables transmission of the test results and the acquired overall assessment factor to the caring places, such as doctors or nursing services, for example.

The structure of the device shown in FIG. 1 is explained in greater detail below with reference to FIG. 2.

Figure 2:
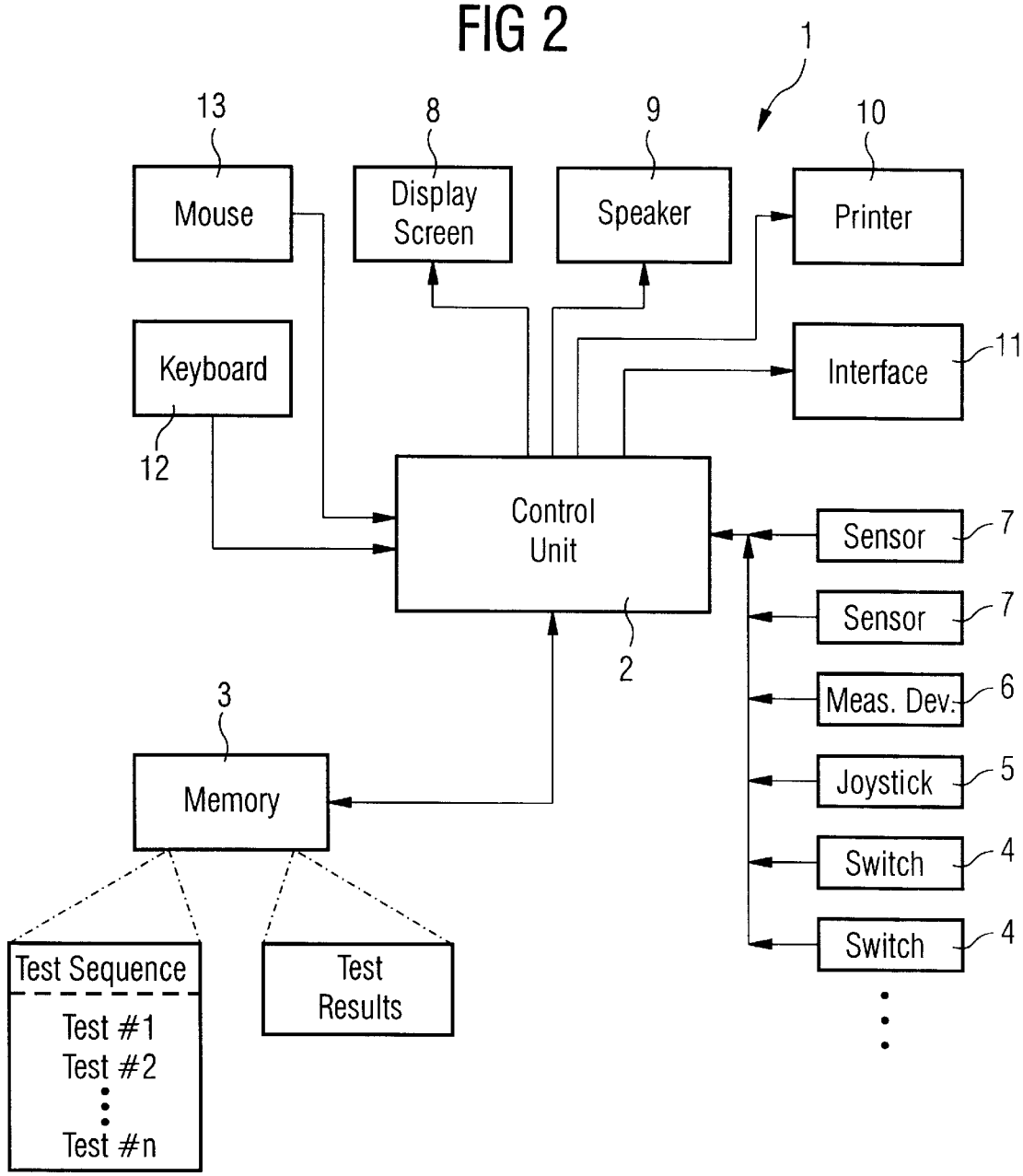
FIG. 2 shows a simplified automated logic diagram, which shows the structure of the device shown in FIG. 1 in greater detail.

FIG. 2 shows the central control unit 2 as a central component of the inventive device, the control unit 2 being coupled with a number of input units 12, 13, a number of output units 8–11 and a number of measuring test devices 4–7. Also, the central control unit 2 is connected to a memory 8 in which test data for carrying out different test exercises 1–n are stored, and in which accumulating test results are stored and in which the overall assessment factors, acquired by the central control unit 2, of the coordinative competence of the respective person can be stored.

FIG. 2 shows a keyboard 12 and a mouse 13 as input units, with the help of which a caregiver or the test person can select the test exercises to be carried out or, subsequently, with the help of which the test results can be manually entered (as warranted via interactive input menus that are displayed on the screen 8 by the central control unit 2).

The output units 8–11 are responsible for the interactive communication between the central control unit 2 and the test person or the caregiver. According to the exemplary embodiment shown in FIG. 2, the input units include the previously mentioned display unit 8, a speaker 9 for speech output, a printer 10 and a remote data transmission interface 11. The printer 10 and the interface 11 particularly serve the purpose of presenting the test results, or the overall assessment factors acquired by the central control unit 2. The relevant data can be transmitted to the place of care, such as a doctor for example, via the interface 11. The display unit 8 and the speaker 9 additionally serve the purpose of providing instructions for carrying out the individual test exercises and are therefore a component of a multi-media auxiliary function, which is offered by the inventive device in order to facilitate the execution of the individual test exercises.

The test media or measuring media 4–7 shown in FIG. 2 serve to automatically acquire the test execution of the individual test exercises and to transmit the corresponding test results to the central control unit 2. According to the exemplary embodiment shown in FIG. 2, these test devices and measuring devices include a number of switches 4 and a number of sensors 7 that can acquire different characteristic values of the respective test person. Acceleration sensors, print sensors, force sensors, length-measuring sensors, path sensors, distance sensors, flex sensors, angle sensors or skin resistance sensors etc. can be employed as sensors 7. The sensors are preferably attached to the body of the test person for carrying out the test. Thus, a balance test, for example, can be carried out using acceleration sensors that are attached to the body of the test person.

Foot switches or hand switches (compare FIG. 1), in particular, can be used as switches 4 that, depending on the type of test, are correspondingly actuated by the test person. Measuring devices, such as blood pressure measuring devices or heart rate measuring devices for example, also can be provided. Such devices continuously monitor the test person and measure specific characteristic values. Other input devices 5, which can be print-based and which, dependent on an actuation by the test person, supply corresponding measuring signals to the central control unit 2, are also useable. Such input devices 5 can, for example, be a touch-screen, a touch-pad or generally conventional keyboard foils. FIG. 2 shows the utilization of a joystick 5 as a specific exemplary embodiment for an input device, the joystick 5 being utilized as a force-feedback input device. Using such a joystick 5, a specific force can be prescribed by the central control unit 2 for the joystick 5 in order to test, for example, the differentiation ability of the test person.

As already explained above, the central control unit 2 is coupled with a memory 3 in which the test data provided for the individual conductible tests are presented (as shown in FIG. 2). The central control unit 2 accesses these data for example when a overall course of test is to be erected and when specific tests corresponding thereto are to be selected from these pre-stored test courses. The memory 3 also serves the purpose of storing the test results acquired by the central control unit 2 and serves the purpose of storing the overall assessment factor, which is calculated in dependency thereof, of the coordinative competence of the respective test person. The reason why it is particularly expedient to store the test results in a memory 3 is that a subsequent analysis of the test results is, later, also possible, and in particular an assessment of the time development of the coordinative competence of the test person can be made.

The tests defined by the test data of the memory 3 can be fashioned such that individual test parameters, such as the number of the test exercises and/or the maximum test time for example, for which the respective test exercise is seen as successful, are initially entered.

The time, which the test person can stand on one leg for example, can be measured as a test for the balance of the test person. The remaining motion, i.e. the swaying motion, of the test person standing can be evaluated. For this purpose, the swaying amplitude or swaying area can be acquired by appropriate sensors. A test wherein an object moving with different speeds is displayed via the screen 8 can be provided as a reaction test for example, whereby the test person must operate, at a specific moment when the object has reached a specific place for example, a corresponding switch 4 or the keyboard 12, or the mouse 13. Subsequently, the device registers the moment of the input of the test person and can calculate the reaction time therefrom. By means of an appropriate succession of tones for example, a time pattern is prescribed for the test person via the speaker 9 for testing the rhythmization ability. The test person must follow this time pattern via an appropriate input device, via a switch 4 or the mouse 13 for example. The prescribed time pattern can also be suppressed during the test execution. Subsequently, the time correlation between the prescribed time pattern and the inputs of the test person is evaluated by the central control unit 2. As a test for eye-foot-coordination ability, a specific task can be prescribed via the screen 8 of the device, which task must be executed via an input device that is to be actuated by the foot of the test person, such as a foot switch 4 or a foot pad for example. Thus, it can be prescribed for the test person via the screen 8, for example, to react at a prescribed moment or to follow a displayed object by actuating a foot switch 4. The accuracy of the execution, such as mistakes when following the object displayed on the screen 8 for example, is thereby evaluated as measure for eye-foot coordination of the test person. Analogously, the eye-hand coordination ability of the test person can be tested, whereby the test person, in this case, must react to displays on the screen 8 with a corresponding actuation of an input device that is to be actuated by hand, such as a mouse 13 or a hand switch 4 for example. In this case, the accuracy of the execution is also evaluated as measure for the eye-hand coordination ability of the test person. A test for the differentiation ability of the test person can also be provided, using (as already mentioned above) a force-feedback input/output device, such as the joystick 5 shown in FIG. 2. The central control unit 2 can prescribe a specific force for the corresponding input device 5 via this force-feedback input/output device. The differentiation ability can be measured with the aid of the pre-defined force applied at this force-feedback-joystick 5.

As the above discussion makes clear, the inventive device enables an automatic quantified measuring of the coordinative competence of a test person, i.e. it enables the measuring of different coordinative abilities, whereby different tests for testing different coordinative abilities can be carried out by means of the inventive device. The device is particularly simple to handle, so that also a test person can carry out the individual tests directly.

Although modifications and changes may be suggested by those skilled in the art, it is the intention of the inventors to embody within the patent warranted hereon all changes and modifications as reasonably and properly come within the scope of our contribution to the art.

We claim as our invention:

1. A device for acquiring and evaluating data representing coordinative abilities of a test person, comprising:
    a control unit adapted for interaction with a user for conducting a plurality of tests to acquire a plurality of datasets respectively representing test results for a plurality of different coordinative abilities of the test person, said control unit processing and combining said datasets to form a quantitative overall assessment of the plurality of different coordinative abilities of the test person; and
    an output unit connected to said control unit supplied with signals representing said overall assessment for generating a surveyable output of said overall assessment.

2. A device as claimed in claim 1 further comprising selection means connected to said control unit for selecting the number of tests to be conducted from among a larger number of prescribed tests.

3. A device as claimed in claim 1 wherein said control unit, dependent on selection criteria, automatically selects the tests comprising said plurality of tests from a prescribed list of tests.

4. A device as claimed in claim 3 wherein said control unit selects a test to be conducted in a random manner from among a plurality of equivalent tests that test the same coordinative ability of the test person upon entry of a designation that said coordinative ability is to be tested.

5. A device as claimed in claim 1 further comprising selection means connected to said control unit for selecting a number of tests to be conducted from among a larger number of prescribed tests, and wherein said control unit automatically selects tests to be conducted from among the tests selected by said selection means.

6. A device as claimed in claim 1 wherein said control unit has access to health data of said test person, and wherein said control unit automatically selects said plurality of tests to be conducted, dependent on said health data, from among a prescribed list of tests.

7. A device as claimed in claim 1 further comprising input means connected to said control unit for allowing said user to enter test results of the respective tests in said plurality of tests.

8. A device as claimed in claim 7 wherein said input means is a component selected from the group consisting of a keyboard and a mouse.

9. A device as claimed in claim 8 further comprising a display unit connected to said control unit on which an interactive input menu is displayed, and wherein said input means interact with said control unit via said interactive input menu.

10. A device as claimed in claim 1 further comprising acquisition means connected to said control unit for automatically acquiring said datasets respectively representing test results of the respective tests in said plurality of tests and for automatically forwarding said datasets to said control unit.

11. A device as claimed in claim 10 wherein said acquisition means comprise at least one component which acquires characteristic values of the test person during execution of said tests, said component being selected from the group consisting of sensors and measuring devices.

12. A device as claimed in claim 10 wherein said acquisition means include a user-actuatable input unit which exhibits a defined force acting against actuation of said input unit and which supplies a signal to said control unit dependent on actuation of said input unit by said test person.

13. A device as claimed in claim 10 wherein said acquisition means include at least one switch which is adapted for actuation by said test person during execution of said tests.

14. A device as claimed in claim 1 further comprising a memory connected to said control unit for storing at least one of individual respective results of said tests in said plurality of tests and said quantitative overall assessment.

15. A device as claimed in claim 14 wherein said memory further stores test sequence data describing tests which are available for said plurality of tests.

16. A device as claimed in claim 1 wherein said output unit comprises an interface for transmitting at least one of said test results and said quantitative overall assessment to a location remote from said control unit.

17. A device as claimed in claim 1 wherein said output unit comprises a display unit for visually presenting at least one of said test results and said quantitative overall assessment.

18. A device as claimed in claim 17 wherein said control unit controls display of said at least one of said test results and said quantitative overall assessment in a time-dependent manner for a predetermined observation period at said display unit.

19. A device as claimed in claim 1 wherein said control unit has access to health data of said test person, and wherein said control unit generates said quantitative overall assessment dependent on said health data.

20. A device as claimed in claim 1 wherein said control unit supplies output instructions via said output unit for conducting the respective tests in said plurality of tests.

21. A device as claimed in claim 1 wherein said control unit cooperates with said output unit for, dependent on a test in said plurality of tests which is currently being conducted, providing a multi-media auxiliary function via said output unit for supporting execution of said test being currently conducted.

22. A device as claimed in claim 1 wherein at least one of said test in said plurality of tests allows testing of at least two different coordinative abilities of said test person.

23. A device as claimed in claim 22 wherein said tests in said plurality of tests are tests selected from the group of tests for testing reactivity, rhythmization ability, eye-hand coordination, eye-foot coordination, balance, and differentiation ability as said coordinative abilities of said test person.

24. A device as claimed in claim 1 wherein one of said test of said plurality of tests comprises a test for testing balance of the test person, and said device further comprising a sensor which measures a time that the test person can stand on one leg.

25. A device as claimed in claim 1 wherein one of said test of said plurality of tests comprises a test for testing balance of the test person, and said device further comprising a sensor which measures movement of said test person while standing.

26. A device as claimed in claim 1 wherein one of said test in said plurality of tests comprises testing reactivity of the test person and further comprising an actuatable input unit connected to said control unit, and wherein said control unit generates an instruction via said output unit for said test person to actuate said input unit and wherein said control unit measures a time following said instruction at which said test person actuates said input unit.

27. A device as claimed in claim 1 wherein one of said test in said plurality of tests comprises a test of rhythmization ability of said test person, and wherein said device further comprises an actuatable input unit, and wherein said control unit, for conducting said test of said rhythmization ability, generates instructions via said output unit for actuating said input unit in a defined time pattern, and wherein said control unit evaluates a time correlation between said defined time pattern and a pattern of actuations of said input unit by said test person.

28. A device as claimed in claim 1 wherein one of said test in said plurality of tests comprises a test of eye-foot coordination of said test person, and wherein said device further comprises a foot-actuated input unit connected to said control unit, and wherein said control unit, via said output unit, instructs said test person to perform a task requiring actuation of said foot-actuated input unit and wherein said control unit evaluates accuracy of execution of said task by said test person.

29. A device as claimed in claim 1 wherein one of said test in said plurality of tests comprises a test of eye-hand coordination of said test person, and wherein said device further comprises a hand-actuated input unit connected to said control unit, and wherein said control unit, via said output unit, instructs said test person to perform a task requiring actuation of said hand-actuated input unit and wherein said control unit evaluates accuracy of execution of said task by said test person.

30. A device as claimed in claim 1 wherein one of said test in said plurality of tests comprises a test of differentiation ability of said test person, and wherein said device further comprises an actuatable input unit having an actuation force defined by said control unit and wherein said control unit, for conducting said test of differentiation ability, instructs the test person via said output device to actuate said input unit and wherein said control unit measures reaction of said test person during actuation of said input unit.

* * * * *